United States Patent [19]
Takita et al.

[11] 4,387,102
[45] Jun. 7, 1983

[54] 4-(N-(3',4'-METHYLENEDIOXYBEN-ZYLIDENE)-AMINOMETHYL)CYCLOHEXANE-1-CARBOXYLIC ACID AND DERIVATIVES THEREOF AND PHARMACEUTICAL COMPOSITION THEREOF

[75] Inventors: Hitoshi Takita; Sakuo Noda; Yutaka Mukaida; Hidetoshi Kobayashi, all of Tokyo, Japan

[73] Assignee: Kureha Kagaku Kogyo Kabushiki Kaisha, Tokyo, Japan

[21] Appl. No.: 331,773

[22] Filed: Dec. 17, 1981

[30] Foreign Application Priority Data

Dec. 22, 1980 [JP] Japan .................................. 55-181707

[51] Int. Cl.³ ..................... A61K 31/36; C07D 317/60
[52] U.S. Cl. ..................................... 424/282; 542/422
[58] Field of Search ......................... 542/422; 424/282

[56] References Cited

U.S. PATENT DOCUMENTS 2,876,220 3/1959 Robertson ........................... 542/222
3,894,051 3/1976 Suh .

FOREIGN PATENT DOCUMENTS 1,544,969 4/1971 United Kingdom .

Primary Examiner—John M. Ford
Assistant Examiner—Bernard Dentz
Attorney, Agent, or Firm—Wegner & Bretschneider

[57] ABSTRACT

A novel compound of 4-[N-(3',4'-methylenedioxybenzylidene) aminomethyl]cyclohexane-1-carboxylic acid or a pharmaceutically acceptable salt or an $C_1$–$C_4$ alkyl ester thereof which has specific pharmacologic activities, a method for preparing thereof and a pharmaceutical composition comprising thereof as an active ingredient are provided.

5 Claims, 3 Drawing Figures

4-(N-(3',4'-METHYLENEDIOXYBENZYLIDENE)-AMINOMETHYL)CYCLOHEXANE-1-CARBOXYLIC ACID AND DERIVATIVES THEREOF AND PHARMACEUTICAL COMPOSITION THEREOF

BACKGROUND AND DETAILED DESCRIPTION OF THE INVENTION

The present invention relates to novel compounds of 4-[N-(3',4'-methylenedioxybenzylidene)aminomethyl]-cyclohexane-1-carboxylic acid or pharmaceutically acceptable salt or a $C_1$–$C_4$ alkyl ester thereof, a method for preparing thereof and a pharmaceutical composition comprising thereof.

It is an object of the invention to provide a novel compound of 4-[N-(3',4'-methylenedioxybenzylidene)aminomethyl]-cyclohexane-1-carboxylic acid or a pharmaceutically acceptable salt or an $C_1$–$C_4$ alkyl ester thereof. An another object of the invention is to provide a method for preparing the novel compound. Furthermore, still another object is to provide a pharmaceutical composition comprising a pharmaceutically effective amount of the novel compound an an active ingredient.

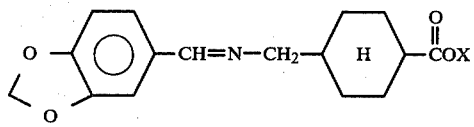

(I)

Figure 1:
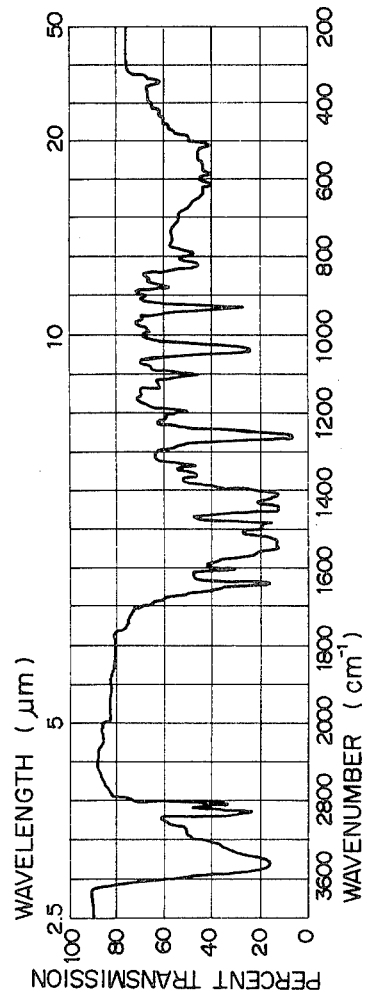
FIG. 1 shows infrared absorption spectra of sodium 4-[N-(3',4'-methylenedioxybenzylidene)aminomethyl]-cyclohexane-1-carboxylate in KBr tablet.

wherein X is hydrogen, alkyl group having 1 to 4 carbon atoms or a pharmaceutically acceptable salt thereof such as sodium salt or ammonium salt thereof. In the general formula (I), the cyclohexane ring includes both trans-, cis-form and mixtures thereof.

The compounds of the invention are low in mammalian toxicity and is useful as an anti-inflammatory, a therapeutic medicine for several diseases and further as an intermediate for preparing pharmaceuticals.

The compound of the invention is preferably prepared by the method described below. Namely, a compound of 3,4-methylenedioxybenzaldehyde represented by the general formula (II)

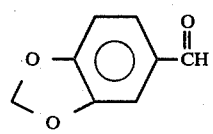

(II)

is brought into reaction with 4-aminomethyl-cyclohexane-1-carboxylic acid represented by the formula (III):

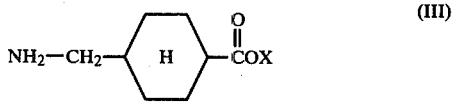

(III)

wherein the cyclohexane ring includes both trans- and/or cis form, and X is the same as in the general formula (I), and the compound of the invention (acid- or ester form) represented by the general formula (I) is obtained by dehydrating-condensation reaction.

The reaction between the compound of the formula (II) and the compound of the formula (III) is carried out in an organic solvent at not higher than 150° C., preferably 0° to 120° C. under atmospheric inert gas. At higher than 150° C., the yield of the desired product is reduced because of various side reactions. Any organic solvent may be used for the reaction if it does not participate in the reaction. A lower alcohol such as methanol or ethanol; benzene; toluene; dimethylformamide; acetonitrile or the like is conventionally used for the reaction.

Since the reaction takes place together with dehydrating, the reaction is carried out in the presence of a dehydrating agent or while removing water formed by the reaction under the reflux of the solvent. An anhydride of a lower alcohol such as an anhydrous methanol or ethanol can be used for the solvent and at the same time for the dehydrating agent.

The compound of the invention (acid- or ester form) is isolated by treating the reaction mixture with a known method after the reaction.

The compound of the invention in salt form is prepared by the conventional method for neutralization by using a base such as hydroxide, carbonate or bicarbonate of an alkali or alkaline earth metal, for example, sodium, potassium, calcium or magnesium, etc., ammonia or primary-, secondary- or tertiary amine or quaternary ammonium salt. For example, a sodium salt is obtained by neutralizing the compound of the invention (in acid form) obtained by the above-mentioned reaction with an alcoholic- or aqueous solution of sodiun hydroxide under atmospheric inert gas at lower than 100° C., usually at 0° to 50° C.

The method mentioned above is only an embodiment of the method for preparing the compound of the invention, and the method of the invention is not restricted to the method as above.

The compound of the invention shows an inhibitory effect on platelet aggregation and/or polynuclear leukocyte migration, and a low acute toxicity, as will be shown in Example 5. Accordingly, the compound of the invention is useful as a remedy for various diseases, such as inflammation, thrombosis, hypertension, asthma or cancer, etc., especially for chronic diseases such as rheumatism or systemic lupus erythematosus (SLE), etc.

When the compound of the invention is used for a pharmaceutical, the salt or ester must be pharmaceutically acceptable.

Furthermore, the compound of the invention may be used as an active ingredient of a phramaceutical composition for the above-mentioned diseases.

The compound of the invention can be administered perorally, rectally or through injection in the various dosage forms as a composition together with a pharmaceutically acceptable carrier and/or an adjuvant. In these cases, a mixture of two or more kinds of the compound of the invention or a mixture together with other pharmaceutically active materials may be used as an active ingredient of a pharmaceutical composition.

The dosage form of the composition may be tablet, sublingual tablet, powder, capsule, troche, aqueous or oily solution, suspension, emulsion, syrup, aqueous or oily injection. An example of the carrier mentioned above is water, gelatin, lactose, starch, pectin, magnesium stearate, stearic acid, talc, vegetable oil, gum arabic, polyalkylene glycol, vaseline, sorbitan tri-oleate, polyoxyethylene-sorbitan mono-oleate, alkylphenol, aliphatic alcohols, polyvinyl pyrrolidone, or the like. In the composition, if necessary, a dulcerant, flavor, tinctorial agent, preservative, salt for osmoregulation or buffer, that is, the conventional pharmaceutical adjuvant may be used together.

The content of the compound of the invention in the pharmaceutical composition may be adequately varied, however, it is 0.01%–100% by weight preferably 0.05%–80% by weight of the composition.

The pharmaceutical composition of the invention is administered into a human or animal parenterally, for example, rectally, through injection (hypodermic, intramuscular or intravenous, or drip), also preferably perorally (for example sublingual etc.).

A dose of the pharmaceutical composition of the invention is 0.1 to 500 mg, preferably 0.5 to 200 mg per day per one kilogram of the body weight in the case of peroral administration into a human, and 0.01 to 200 mg, preferably 0.1 to 100 mg in the case of parenteral administration, and the pharmaceutics is administered one to four times a day. However the dose of the pharmaceutical composition depends on age, individuality, condition of a disease etc. of a human or animal, and the dose out of the above-mentioned range may be used.

The properties, method for preparation and pharmacologic effects of the compound of the invention are concretely described while referring to the examples.

EXAMPLE 1

Preparation of 4-[N-(3',4'-methylenedioxybenzylidene)aminomethyl]-cyclohexane-1-carboxylic acid:

Into 30 ml of dehydrated and purified methanol, 1.91 g (12.72 m mol) of 3,4-methylenedioxybenzaldehyde was dissolved, and the resulting solution was dropped into 2.00 g (12.72 m mol) of trans-4-aminomethyl-cyclohexane-1-carboxylic acid under atmospheric nitrogen, and the resulting mixed solution was refluxed while stirring for 3 hours.

Small amount of insoluble materials were removed by filtration, and the filtrate was concentrated and left overnight at a room temperature. Educing crystals were collected by filtration, washed with methanol and vacuum-dried. 1.22 g of 4-[N-(3',4'-methylenedioxybenzylidene)aminomethyl]cyclohexane-1-carboxylic acid melting at 146° to 147° C. (according to hot plate method) was obtained with the yield of 33.2%.

The characteristics of the compound of the invention thus obtained were as follows:

(1) Elementary analytical data: Found(%) C: 66.30, H: 6.70, N: 4.90. Calcd.(%) as $C_{16}H_{19}O_4N$, C: 66.42, H: 6.62, N: 4.84.

(2) NMR: $\delta = 1.03 \sim 1.90$ (9H, m), 1.99~2.13(1H), 3.36(2H, d), 6.06(2H, s), 6.95(1H, d), 7.19(1H, d), 7.28(1H, s) and 8.15(1H, s).

EXAMPLE 2

Preparation of sodium 4-[N-(3',4'-methylenedioxybenzylidene)-aminomethyl]-cyclohexane-1-carboxylate:

Into 100 ml (10.0 m mol) of 0.1 N aqueous solution of sodium hydroxide, 2.893 g (10.0 m mol) of 4-[N-(3',4'-methylenedioxybenzylidene)aminomethyl]cyclohexane-1-carboxylic acid obtained in Example 1 was added under atmospheric nitrogen, and the resulting mixture was stirred for 2 hours at room temperature to obtain a yellow solution. The yellow solution was filtered and then freeze-dried, and 3.472 g of sodium 4-[N-(3',4'-methylenedioxybenzylidene)aminomethyl]cyclohexane-1-carboxylate was obtained with the yield of 100%.

The characteristics of the sodium salt thus obtained were as follows:

(1) Melting point (according to capillary method): 270.0° to 273.0° C. (decomposed).

(2) Elementary analytical data: Found(%) C: 55.60, H: 6.20, N: 4.10; Calcd.(%) as $C_{16}H_{18}NO_4\cdot Na\cdot 2H_2O$ C: 55.32, H: 6.38, N: 4.03.

(3) Infrared absorption spectrum (KBr Tablet): Referred to FIG. 1.

EXAMPLE 3

Preparation of methyl 4-[N-(3',4'-methylenedioxybenzylidene)aminomethyl]-cyclohexane-1-carboxylate:

(a) After dropping 12.5 g of thionyl chloride into 82 ml of icewater-cooled methanol while stirring well, the cooling bath for methanol was removed, and then after adding 11.0 g of trans-4-aminomethylcyclohexane-1-carboxylic acid to the mixture, the thus formed mixture was heated for 5 hours at 50° to 60° C. Then, the reaction mixture was filtered while warm and the filtrate was concentrated to about 25 ml under a reduced pressure. The crystals educing on adding 140 ml of ether to the concentrated solution were collected by filtration after icewater-cooling and recrystallized from a mixture of methanol and ether to obtain 13.4 g of colourless plate-like crystals of methyl trans-4-aminomethylcyclohexane-1-carboxylate hydrochloride in a yield of 92.1% giving the following elementary analytical data:

Elementary analytical data: Found(%) C: 51.70, H: 9.00, N: 6.80. Calcd.(%) as $C_9H_{18}NO_2Cl$ C: 52.04, H: 8.74, N: 6.74.

(b) After neutralizing 4.43 g of the thus obtained methyl trans-4-aminomethylcyclohexane-1-carboxylate hydrochloride with 20 ml of 1 N sodium hydroxide solution, the solution was extracted three times with each 30 ml of ethyl acetate. The extract after washing with water was dried with anhydrous sodium sulfate, and the solvent in the filtrate obtained by filtration of the dried extract was removed by evaporation under a reduced pressure in a warm water bath to obtain 2.70 g of a colourless liquid of methyl trans-4-aminomethylcyclohexane-1-carboxylate in a yield of 78.9% giving the following elementary analytical data:

Elementary analytical data: Found(%) C: 62.90, H: 10.10, N: 7.90. Calcd.(%) as $C_9H_{17}NO_2$ C: 63.12, H: 10.01, N: 8.18.

(c) After dissolving 1.60 g (9.34 m mol) of the thus obtained methyl ester and 1.40 g (9.34 m mol) of piperonal into 40 ml of methanol, the solution was refluxed for 16 hours, and then, after removing the solvent from the solution under a reduced pressure in a warm water bath, the residue was dissolved in 40 ml of n-hexane. After filtering the solution while warm, the filtrated was subjected to recrystallization to obtain 2.68 g of colourless acicular crystals of methyl 4-[N-(3',4'-methylenedioxybenzylidene)aminomethyl]cyclohexane-1-carboxylate in a yield of 94.7% melting at 55.0° to 58.0° C. (according to capillary method) and giving the following elementary analytical data and the infrared absorption spectrum as follows:

(1) Elementary analytical data: Found(%) C: 67.20, H: 7.10, N: 4.60. Calcd.(%) as $C_{17}H_{21}NO_4$ C: 67.31, H: 6.98, N: 4.62.

Figure 2:
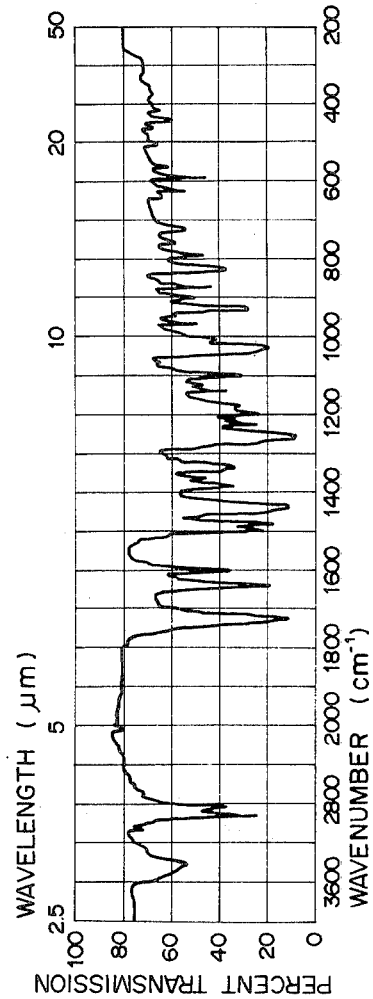
FIG. 2 shows infrared absorption spectra of methyl 4-[N-(3',4'-methylenedioxybenzylidene)aminomethyl]-cyclohexane-1-carboxylate in KBr tablet.

(2) Infrared absorption spectrum (KBr Tablet) Referred to FIG. 2.

EXAMPLE 4

Preparation of ethyl 4-[N-(3',4'-methylenedioxybenzylidene)aminomethyl]-cyclohexane-1-carboxylate In a similar manner except for using ethanol instead of methanol in Example 3, ethyl trans-4-aminomethyl-cyclohexane-1-carboxylate hydrochloride, ethyl trans-4-aminoethylcyclohexane-1-carboxylate and ethyl 4-[N-(3',4'-methylenedioxybenzylidene)aminomethyl]cyclohexane-1-carboxylate were synthesized in the above-mentioned order.

The respective physical properties of the products are as follows:

(a) Ethyl trans-4-aminomethylcyclohexane-1-carboxylate hydrochloride:

Yield: 14.2 g (91.6%)

Melting point (according to capillary method): 187°~188° C.

Elementary analytical data: Found(%) C: 54.20, H: 9.10, N: 6.40. Calcd.(%) as $C_{10}H_{20}NO_2Cl$ C: 54.16; H: 9.09; N: 6.32.

(b) Ethyl trans-4-aminomethylcyclohexane-1-carboxylate:

Yield: 3.10 g (83.8%)

Elementary analytical data: Found(%) C: 64.80, H: 10.00, N: 7.80 Calcd.(%) as $C_{10}H_{19}NO_2$ C: 64.83, H: 10.34; N: 7.56.

(c) Ethyl 4-[N-(3',4'-methylenedioxybenzylidene)aminomethyl]cyclohexane-1-carboxylate:

(1) Yield: 2.63 g (83.0%)

(2) Melting point: 72.5°~73.5° C. (according to capillary method)

(3) Elementary analytical data: Found(%) C: 68.20, H: 7.30, N: 4.40. Calcd.(%) as $C_{18}H_{23}NO_4$ C: 68.12, H: 7.30, N: 4.41.

Figure 3:
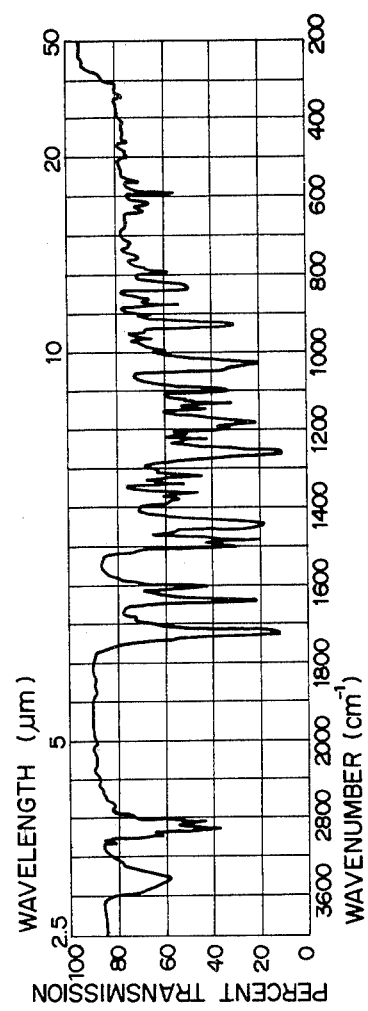
FIG. 3 shows infrared absorption spectra of ethyl 4-[N-(3',4'-methylenedioxybenzylidene)aminomethyl]-cyclohexane-1-carboxylate in KBr tablet. The novel compound of 4-[N-(3',4'-methylenedioxybenzylidene)aminomethyl]cyclohexane-1-carboxylic acid (hereinafter referred to as the compound of the invention) is represented by the general formula (I)

(4) Infrared absorption spectrum (KBr Tablet): Referred to FIG. 3.

EXAMPLE 5

Tests for inhibition of blood platelet aggregation and for acute toxicity of sodium 4-[N-(3',4'-methylenedioxybenzylidene)aminomethyl]-cyclohexane-1-carboxylate:

(5-1) Test for inhibition of platelet aggregation was carried out while using rabbit's platelets, an aqueous physiological saline solution of sodium 4-[N-(3',3'-methylenedioxybenzylidene)aminomethyl]cyclohexane-1-carboxylate and 400 micromols of sodium arachidonate as the aggregation agent in a platelet aggregation tracer PAT 4A (made by Niko Bioscience Company, Japan) as the testing apparatus.

As the results of the test, the percents (%) of inhibition of the aggregation of the platelets by sodium arachidonate due to sodium 4-[N-(3',4'-methylenedioxybenzylidene)aminomethyl]cyclohexane-1-carboxylate at its respective concentrations of 500, 1000 and 1500 micromols were found to be 30, 75 and 100, respectively.

(5-2) Acute oral toxicity test were carried out by orally administering aqueous solutions of sodium 4-[N-(3',4'-methylenedioxybenzylidene)aminomethyl]cyclohexane-1-carboxylate to groups of female JCL-ICR mice of five weeks after birth. As the results of the test, no abnormality was found on the mouse administered with 3000 mg/kg of the test compound.

EXAMPLE 6

Tests for inhibition of migration of polymorphonuclear leukocytes to the inflammatory region Tests for inhibition of migration of polymorphonuclear leukocytes to the inflammatory region due to sodium 4-[N-(3',4'-methylenedioxybenzylidene)aminomethyl]cyclohexane-1-carboxylate were carried out following the method of Granuloma-CMC-Pouch (refer to Ishikawa et al. J. Pharmaceut. Soc. Jap., Vol. 88, page 1472, 1968).

Namely, after cutting the hair on the back of male rats (Donryu, body weight: 150 g), 5 ml of air was injected subcutaneously into the hair-cut region and further, 5 ml of aqueous 2% (W/V) solution of sodium carboxymethyl cellulose (CMC) at 37° C. was injected.

Specimens of the liquid (0.5 ml, each) effused into the pouch were collected at 3, 6 and 24 hours after 2% CMC solution were injected respectively and then the number of polymorphonuclear leukocytes in the specimen was counted after staining to determine the rate of inhibition of migration of the polymorpholeukocyte as compared to the number of the polymorpholeukocytes in the specimen collected from control animal to which the aqueous CMC solution was injected after air injection.

In this test, sodium 4-[N-(3',4'-methylenedioxybenzylidene)aminomethyl]cyclohexane-1-carboxylate was orally administered as a solution in aqueous physiological saline solution at a dose of 100 mg/kg at the time of injecting the solution of CMC, and as a control, 1 mg/kg of indomethacin was orally administered to other rat with cut hair at the time of injecting the solution of CMC. The results of this test are shown in Table below.

TABLE

| | Number of polymorphonuclear leukocytpes at 3, 6 and 24 hours | | | | | |
|---|---|---|---|---|---|---|
| | 3 hours of injection of CMC | | 6 hours of injection of CMC | | 24 hours of injection of CMC | |
| Compound | Number/mm$^3$ | R.I. (%)* | Number/mm$^3$ | R.I. (%) | Number/mm$^3$ | R.I. (%) |
| Present compound** | $1.9 \times 10^3$ | 46 | $2.7 \times 10^3$ | 54 | $10.1 \times 10^3$ | 32 |
| Indomethacin*** | $2.3 \times 10^3$ | 34 | $4.1 \times 10^3$ | 31 | $10.8 \times 10^3$ | 28 |

TABLE-continued

| | Number of polymorphonuclear leukocytpes at 3, 6 and 24 hours | | | | | |
|---|---|---|---|---|---|---|
| | 3 hours of injection of CMC | | 6 hours of injection of CMC | | 24 hours of injecttion of CMC | |
| Compound | Number/mm³ | R.I. (%)* | Number/mm³ | R.I. (%) | Number/mm³ | R.I. (%) |
| Control | 3.5 × 10³ | — | 5.9 × 10³ | — | 14.9 × 10³ | — |

Notes:
R.I. (%)* means the inhibitory rate pf migration of polymorphonuclear leukocytes into the pouch as compared to control.
Present compound**: Sodium 4-[N—(3',4'-methylenedioxybenzylidene)aminomethyl]cyclohexane-1-carboxylate orally administered once at 100 mg/kg, at the time of injecting sodium CMC.
Indomethacin***: Orally administered once at 10 mg/kg, at the time of injecting sodium CMC.

What is claimed is:

1. A compound represented by the formula (I)

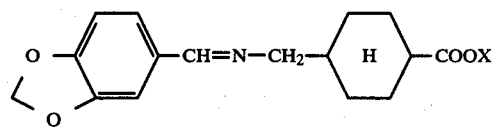

(I)

wherein X is hydrogen, alkyl group having 1 to 4 carbon atoms or a pharmaceutically acceptable salt thereof.

2. The compound of claim 1, which is 4-[N-(3',4'-methylenedioxybenzylidene)aminomethyl]cyclohexane-1-carboxylic acid.

3. The compound of claim 1, which is methyl 4-[N-(3',4'-methylenedioxybenzylidene)aminomethyl]cyclohexane-1-carboxylate.

4. The compound of claim 1, which is ethyl 4-[N-(3',4'-methylenedioxybenzylidene)aminomethyl]cyclohexane-1-carboxylate.

5. A pharmaceutical composition in dosage unit form having an inhibitory effect on platelet aggregation and polynuclear leukocyte migration, comprising an amount of a compound of claim 1 effective for inhibition of platelet aggregation and polynuclear leukocyte migration and a pharmaceutically acceptable carrier therefore.